United States Patent
Imada et al.

(10) Patent No.: US 9,469,592 B2
(45) Date of Patent: Oct. 18, 2016

(54) RADICALLY CURABLE COMPOUND, METHOD FOR PRODUCING RADICALLY CURABLE COMPOUND, RADICALLY CURABLE COMPOSITION, CURED PRODUCT OF THE SAME, AND RESIST-MATERIAL COMPOSITION

(71) Applicant: DIC Corporation, Tokyo (JP)

(72) Inventors: Tomoyuki Imada, Ichihara (JP); Takakazu Kage, Ichihara (JP); Dongmi Shin, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 14/415,337

(22) PCT Filed: Jun. 25, 2013

(86) PCT No.: PCT/JP2013/067344
§ 371 (c)(1),
(2) Date: Jan. 16, 2015

(87) PCT Pub. No.: WO2014/017236
PCT Pub. Date: Jan. 30, 2014

(65) Prior Publication Data
US 2015/0166459 A1 Jun. 18, 2015

(30) Foreign Application Priority Data

Jul. 25, 2012 (JP) ................................ 2012-164813

(51) Int. Cl.
*C08L 69/00* (2006.01)
*C07C 69/54* (2006.01)
(Continued)

(52) U.S. Cl.
CPC .............. *C07C 69/54* (2013.01); *C07C 37/002* (2013.01);
(Continued)

(58) Field of Classification Search
CPC ....... C07C 69/54; C07C 37/20; C07C 39/16; C07C 67/14
See application file for complete search history.

(56) References Cited

U.S. PATENT DOCUMENTS

| | | |
|---|---|---|
| 4,774,274 A | 9/1988 | Takata et al. |
| 2005/0095541 A1 | 5/2005 | Ando et al. |

FOREIGN PATENT DOCUMENTS

| | | | |
|---|---|---|---|
| EP | 0251724 A2 | 1/1988 | |
| JP | 09-157340 A | 6/1997 | |
| JP | 2004054002 | * 2/2004 | ............ G03C 1/498 |

OTHER PUBLICATIONS

International Search Report mailed Sep. 17, 2013, issued for PCT/JP2013/067344.

(Continued)

*Primary Examiner* — Shane Fang
(74) *Attorney, Agent, or Firm* — Locke Lord LLP

(57) ABSTRACT

Provided is a positive photoresist composition excellent in terms of heat resistance. A radically curable compound is represented by a general formula (1) below (where $R^1$, $R^2$, and $R^3$ each independently represent an alkyl group having 1 to 8 carbon atoms; m and n each independently represent an integer of 1 to 4; p represents an integer of 0 to 4; X, Y, and Z each independently represent an acryloyloxy group, a methacryloyloxy group, or a hydroxy group, and at least one of X, Y, and Z represents an acryloyloxy group or a methacryloyloxy group; and t represents 1 or 2).

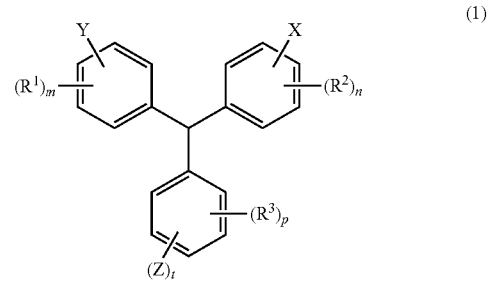

(1)

20 Claims, 1 Drawing Sheet

(51) Int. Cl.

| | |
|---|---|
| *C08G 8/30* | (2006.01) |
| *C08F 222/10* | (2006.01) |
| *C07C 37/20* | (2006.01) |
| *C07C 67/14* | (2006.01) |
| *C07C 37/00* | (2006.01) |
| *C08F 22/14* | (2006.01) |
| *C09D 4/00* | (2006.01) |

(52) U.S. Cl.
CPC ............... *C07C 37/20* (2013.01); *C07C 67/14* (2013.01); *C08F 22/14* (2013.01); *C08F 222/1006* (2013.01); *C08G 8/30* (2013.01); *C09D 4/00* (2013.01)

(56) References Cited

OTHER PUBLICATIONS

Supplementary European Search Report dated Mar. 8, 2016, issued for the corresponding European patent application No. 13822504.0.

\* cited by examiner

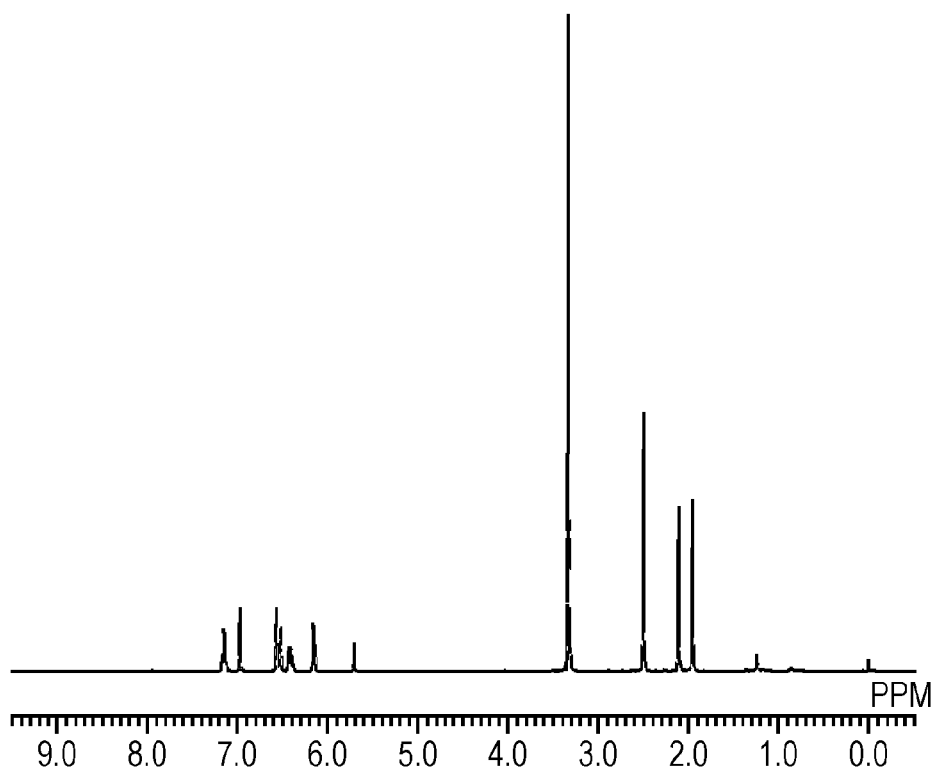

RADICALLY CURABLE COMPOUND, METHOD FOR PRODUCING RADICALLY CURABLE COMPOUND, RADICALLY CURABLE COMPOSITION, CURED PRODUCT OF THE SAME, AND RESIST-MATERIAL COMPOSITION

TECHNICAL FIELD

The present invention relates to a radically curable compound that provides a cured product excellent in terms of heat resistance.

BACKGROUND ART

In recent years, electronic devices have undergone remarkable technical advances and integrated circuits having a higher density and higher performance have been rapidly developed. In response to such developments, printed wiring boards have come to have a higher density, more highly integrated wiring, and surface-mounted components. Such printed wiring boards also need to have a higher accuracy and higher performance than before. In response to such developments of integrated circuits having a higher density and higher performance, there have been studies on improvements in the performance of solder resist serving as a main material of integrated circuits. Build-up boards and the like having fine wiring therein still have a problem in that cracking occurs at the interface between solder resist and sealing resin, which is referred to as popcorning. Thus, there has been a demand for a solder resist having higher heat resistance.

With an increase in the degree of integration of integrated circuits, nanoimprint lithography has been attracting attention as a process for ultrafine patterning allowing a linewidth of 20 nm or less. This nanoimprint lithography is broadly divided into thermal nanoimprint lithography and photo nanoimprint lithography. The thermal nanoimprint lithography is performed in the following manner: a polymer resin is heated to a glass transition temperature or higher to be softened; a mold is pressed into this resin; and the mold is released from the resin having cooled, so that a fine structure is transferred to the resin on a substrate. Thus, nano-patterns can be formed at relatively low costs. The thermal nanoimprint lithography is expected to be applied in various fields. However, the thermal nanoimprint lithography requires softening of such a polymer resin by heating and polymer resins having a high glass transition temperature are difficult to use. Thus, the thermal nanoimprint lithography is difficult to apply to the electric and electronic field in which higher heat resistance has been required in recent years.

On the other hand, the photo nanoimprint lithography employs photo-curing of a composition upon irradiation with light. The photo nanoimprint lithography does not require heating of a molding material to which a pattern is transferred during pressing. Thus, imprinting can be achieved at room temperature. Photo-curable resins used for the photo nanoimprinting are of a radical polymerization type, an ionic polymerization type, and a hybrid of these types. Curable compositions of any of these types can be used for nanoimprinting. However, photo-curable compositions of the radical polymerization type, of which there is a wide choice of viable materials, have been commonly studied.

In the cases where materials for nanoimprinting are used for protective films and spacers for thin-film transistors and liquid crystal color filters in liquid crystal displays and for permanent films used for fine processing of other members for liquid crystal display apparatuses, cured products of the materials for nanoimprinting need to be excellent in terms of mechanical property, transparency, light resistance, heat resistance, or the like and, in particular, need to have very high heat resistance. Known examples of such a material that can provide cured products having high heat resistance are epoxy (meth)acrylate resins having a biphenyl skeleton (for example, refer to Patent Literature 1). However, these resins do not have the high heat resistance that has been required in recent years.

CITATION LIST

Patent Literature

PTL 1: Japanese Unexamined Patent Application Publication No. 9-157340

SUMMARY OF INVENTION

Technical Problem

An object of the present invention is to provide a radically curable compound that provides a cured product excellent in terms of heat resistance and another object is to provide a method for producing the compound.

Solution to Problem

The inventors of the present invention performed thorough studies. As a result, the inventors have found, for example, the following findings: a cured product has very high heat resistance, the cured product being obtained by curing a compound having a structure that is provided by a reaction between a trifunctional phenol having a specific structure and a (meth)acrylic acid halide; and such a method allows easy production of the compound. Thus, the inventors have accomplished the present invention.

Specifically, the present invention provides a radically curable compound represented by a general formula (1) below

[Chem. 1]

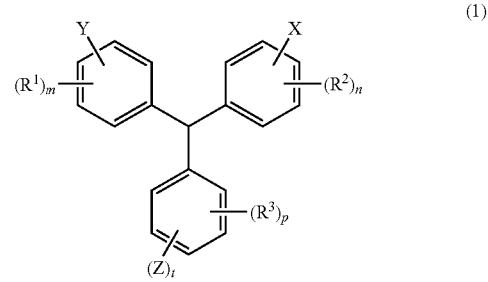

(where $R^1$, $R^2$, and $R^3$ each independently represent an alkyl group having 1 to 8 carbon atoms; m and n each independently represent an integer of 1 to 4; p represents an integer of 0 to 4; X, Y, and Z each independently represent an acryloyloxy group, a methacryloyloxy group, or a hydroxy group, and at least one of X, Y, and Z represents an acryloyloxy group or a methacryloyloxy group; and t represents 1 or 2).

In addition, the present invention provides a method for producing a radically curable compound, the method including causing polycondensation between an alkyl-substituted phenol (a1) and an aromatic aldehyde (a2) having a hydroxy group on a benzene ring to prepare a polycondensate (A) represented by a general formula (3) below

[Chem. 2]

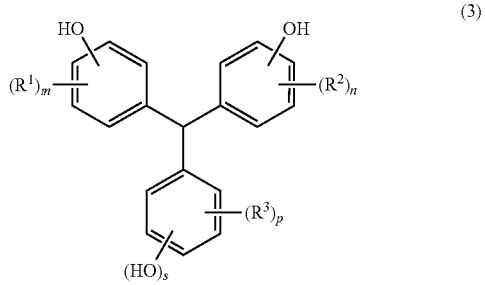

(where $R^1$, $R^2$, and $R^3$ each independently represent an alkyl group having 1 to 8 carbon atoms; m and n each independently represent an integer of 1 to 4; p represents an integer of 0 to 4; and s represents 1 or 2); and subsequently causing a reaction between the polycondensate and a (meth)acrylic acid halide (B).

In addition, the present invention provides a radically curable compound obtained by the above-described production method.

In addition, the present invention provides a radically curable composition including the above-described radically curable compound.

In addition, the present invention provides a cured product obtained by curing the above-described radically curable composition with an active energy ray or heat.

In addition, according to the present invention, a resist-material composition includes the above-described radically curable composition.

Advantageous Effects of Invention

A radically curable compound according to the present invention can provide a cured product having heat resistance on a very high level. Accordingly, a radically curable compound according to the present invention can be used as a solder resist material and a material for nanoimprinting that are required to have high heat resistance. A radically curable compound according to the present invention is a material that is photo-curable and can be used to form a shape by light and hence can also be used for a material for a mold of the thermal nanoimprint lithography. In a case where a thermoplastic resin used as resist in the thermal nanoimprint lithography is a high-heat-resistant electric/electronic-material engineering plastic having a glass transition temperature (Tg) of more than 200° C. such as polyphenylene ether (PPE), this plastic is subjected to a softening treatment at a temperature of 300° C. or more. In this case, a cured product of a radically curable compound according to the present invention has very high heat resistance and hence can be used as a material for the mold.

A radically curable compound according to the present invention has benzene rings at a high density and hence has a more rigid skeleton and the cured product thereof has high heat resistance. In addition, because of the rigid skeleton, the cured product is also excellent in terms of mechanical property (impact resistance) and has high water resistance and particularly a high hardness. Accordingly, a radically curable compound according to the present invention can be suitably used as, for example, a hard-coating material for films formed of triacetylcellulose (TAC) or the like used as polarizing plates of liquid crystal displays of televisions, video cameras, computers, cellular phones, or the like, the displays requiring high surface hardness; a hard-coating material for transparent protective films that protect the surfaces of various displays such as liquid crystal displays, plasma displays, or organic EL displays; or a hard-coating material for optical lenses. In addition, a production method according to the present invention allows easy production of a radically curable compound according to the present invention.

BRIEF DESCRIPTION OF DRAWING

FIG. 1 is a $^1$H-NMR spectrum chart of a radically curable compound (1) obtained in Example 1.

DESCRIPTION OF EMBODIMENTS

A radically curable compound according to the present invention has a molecular structure represented by a general formula (1) below

[Chem. 3]

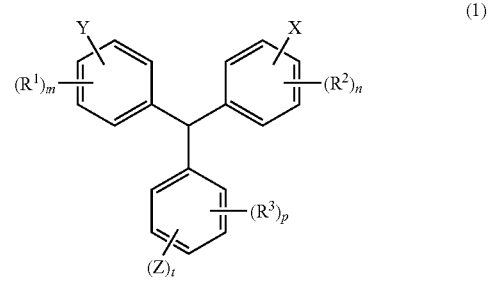

(where $R^1$, $R^2$, and $R^3$ each independently represent an alkyl group having 1 to 8 carbon atoms; m and n each independently represent an integer of 1 to 4; p represents an integer of 0 to 4; X, Y, and Z each independently represent an acryloyloxy group, a methacryloyloxy group, or a hydroxy group, and at least one of X, Y, and Z represents an acryloyloxy group or a methacryloyloxy group; and t represents 1 or 2).

In the general formula (1), $R^1$, $R^2$, and $R^3$ each independently represent an alkyl group having 1 to 8 carbon atoms: specifically, for example, a methyl group, an ethyl group, a propyl group, an isopropyl group, a n-butyl group, a t-butyl group, a pentyl group, a hexyl group, a heptyl group, or an octyl group. Such alkyl groups allow high heat resistance of cured products. $R^1$, $R^2$, and $R^3$ preferably each represent a methyl group among these alkyl groups because molecular motion is suppressed to allow high rigidity of the molecules; cured products have higher heat resistance; electron donation to phenolic benzene nuclei is allowed; and industrial availability is high.

In the general formula (1)), m and n each independently represent an integer of 1 to 4 and p represents an integer of 0 to 4. In particular, an integer of 1 to 3 is preferred because of, for example, high reactivity, ease of design of the reaction, or ease of industrial availability of raw materials.

In the general formula (1), X, Y, and Z each independently represent an acryloyloxy group, a methacryloyloxy group, or a hydroxy group. Here, in a case where t in the general formula (1) represents 2, two Z's in the molecule may be the same or different from each other.

At least one of X, Y, and Z above represents an acryloyloxy group or a methacryloyloxy group. More preferably, X, Y, and Z each represent an acryloyloxy group or a methacryloyloxy group because the compound has high curability. In a case where X, Y, and Z represent an acryloyloxy group, the radically curable compound has a high curing rate and provides cured products having high adhesion to substrates. On the other hand, in a case where X, Y, and Z represent a methacryloyloxy group, the radically curable compound tends not to undergo shrinkage on curing and provides cured products having high adhesion to substrates.

In the general formula (1), t represents an integer of 1 or 2; t preferably represents 1 because of ease of industrial availability of raw materials or ease of design of the reaction.

In the general formula (1), X and Y are bonded preferably at para positions with respect to the methine group that bonds three aromatic rings together because cured products having high heat resistance can be obtained. Thus, a preferred form of the radically curable compound represented by the general formula (1) is a radically curable compound represented by a general formula (2) below

[Chem. 4]

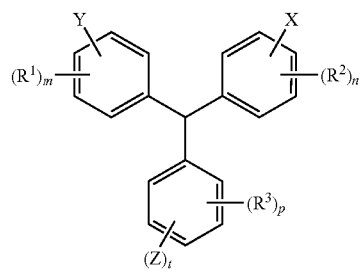

(2)

(where $R^1$, $R^2$, and $R^3$ each independently represent an alkyl group having 1 to 8 carbon atoms; m and n each independently represent an integer of 1 to 4; p represents an integer of 0 to 4; and X, Y, and Z each independently represent an acryloyloxy group, a methacryloyloxy group, or a hydroxy group, and at least one of X, Y, and Z represents an acryloyloxy group or a methacryloyloxy group).

Specifically, the radically curable compound represented by the general formula (1) may have a molecular structure represented by any one of the following structural formulae (1-1) to (1-14).

[Chem. 5]

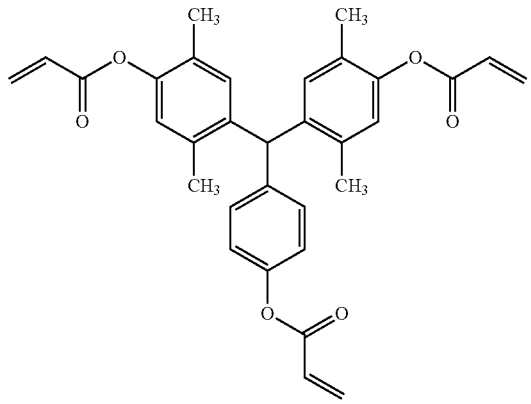

(1-1)

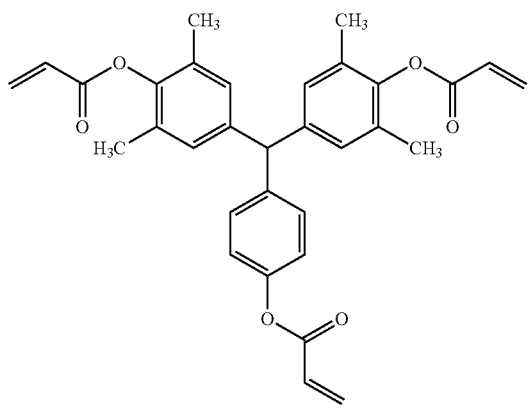

(1-2)

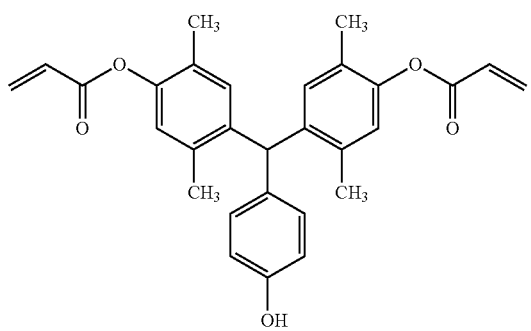

(1-3)

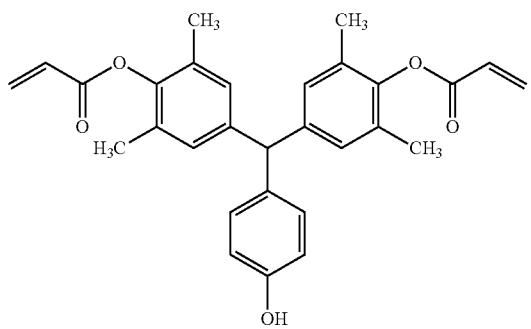

(1-4)

(1-5)
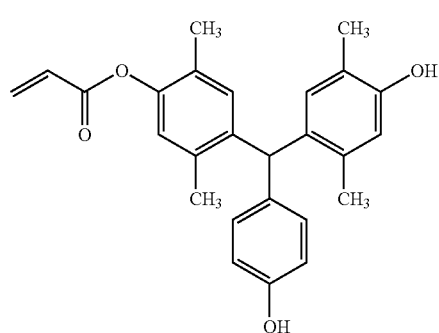
(1-6)
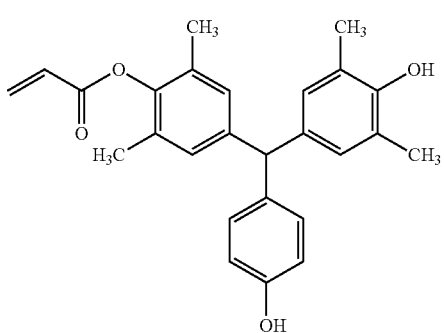
[Chem. 6]
(1-7)
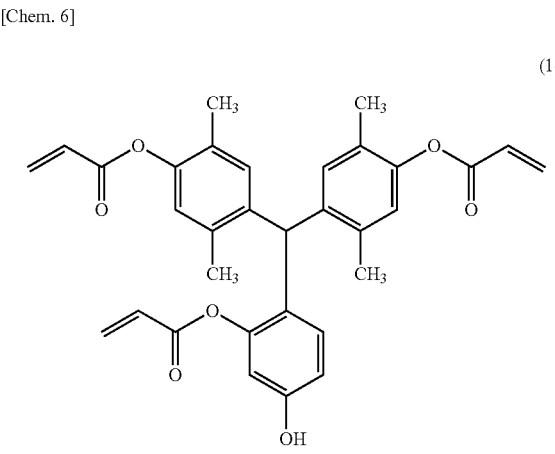
(1-8)
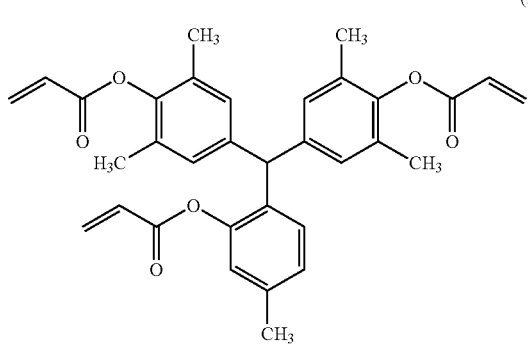
(1-9)
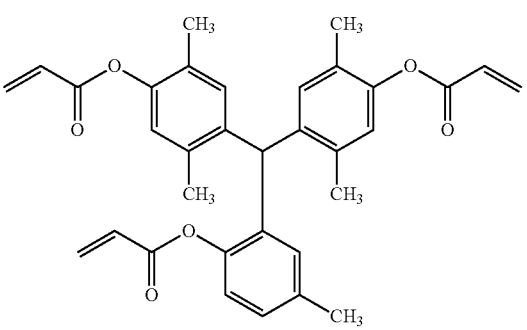
(1-10)
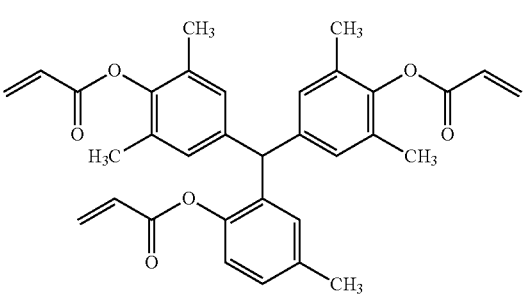
(1-11)
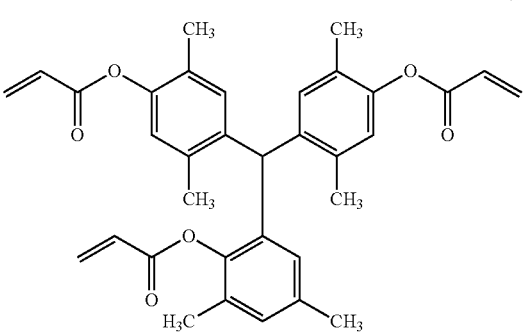
(1-12)
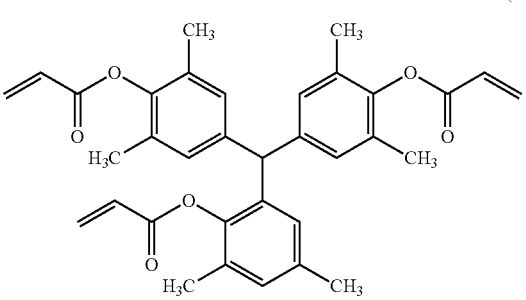

(1-13)

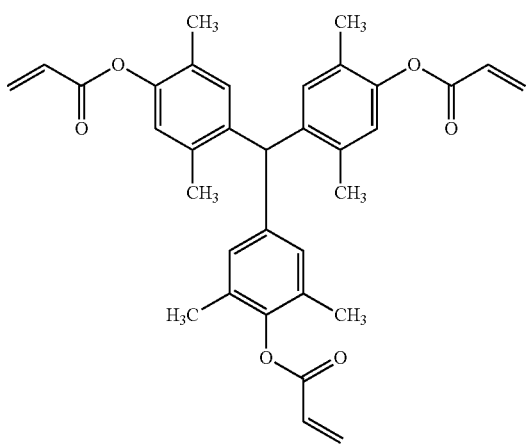

(1-14)

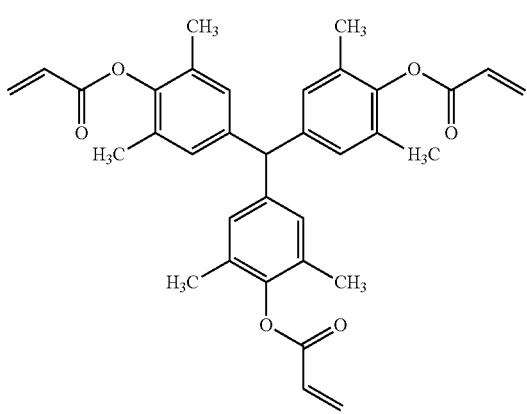

A radically curable compound according to the present invention can be easily produced by, for example, a method including causing polycondensation between an alkyl-substituted phenol (a1) and an aromatic aldehyde (a2) having a hydroxy group on a benzene ring to prepare a polycondensate (A) represented by a general formula (3) below

[Chem. 7]

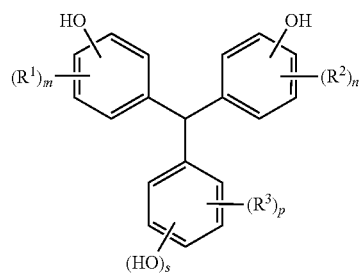

(3)

(where $R^1$, $R^2$, and $R^3$ each independently represent an alkyl group having 1 to 8 carbon atoms; m and n each independently represent an integer of 1 to 4; p represents an integer of 0 to 4; and s represents 1 or 2); and subsequently causing a reaction between the polycondensate and a (meth)acrylic acid halide (B). Note that, in the present invention, "(meth)acrylic acid" denotes one or both of "acrylic acid" and "methacrylic acid".

The alkyl-substituted phenol (a1) is a compound in which a part of or all the hydrogen atoms bonded to the aromatic ring of phenol are replaced by alkyl groups. Specific examples of such an alkyl group include an alkyl group having 1 to 8 carbon atoms such as a methyl group, an ethyl group, a propyl group, an isopropyl group, a n-butyl group, a t-butyl group, a pentyl group, a hexyl group, a heptyl group, or an octyl group. In particular, a methyl group is preferred.

Examples of the alkyl-substituted phenol (a1) include monoalkyl phenols such as o-cresol, m-cresol, p-cresol, o-ethylphenol, m-ethylphenol, p-ethylphenol, p-octylphenol, p-t-butylphenol, o-cyclohexylphenol, m-cyclohexylphenol, and p-cyclohexylphenol; dialkyl phenols such as 2,5-xylenol, 3,5-xylenol, 3,4-xylenol, 2,4-xylenol, and 2,6-xylenol; and trialkyl phenols such as 2,3,5-trimethylphenol and 2,3,6-trimethylphenol. Among these alkyl-substituted phenols, because of high heat resistance, preferred are those in which the aromatic ring of phenol is substituted with two alkyl groups; in particular, preferred are 2,5-xylenol and 2,6-xylenol. These alkyl-substituted phenols (a1) may be used alone or in combination of two or more thereof.

Examples of the aromatic aldehyde (a2) having a hydroxy group on a benzene ring include hydroxybenzaldehydes such as 2-hydroxybenzaldehyde, 3-hydroxybenzaldehyde, and 4-hydroxybenzaldehyde; dihydroxybenzaldehydes such as 2,4-dihydroxybenzaldehyde and 3,4-dihydroxybenzaldehyde; and alkyl-group-containing hydroxybenzaldehydes such as 2-hydroxy-4-methylbenzaldehyde, 2-hydroxy-5-methylbenzaldehyde, 2-hydroxy-3,5-dimethylbenzaldehyde, and 4-hydroxy-3,5-dimethylbenzaldehyde. Among these aromatic aldehydes, because of ease of industrial availability and being highly balanced in terms of heat resistance and alkaline solubility, preferred are hydroxybenzaldehydes; in particular, more preferred are 4-hydroxybenzaldehyde and 4-hydroxy-3,5-dimethylbenzaldehyde. These aromatic aldehydes (a2) may be used alone or in combination of two or more thereof.

The halide of the (meth)acrylic acid halide (B) may correspond to fluorine, chlorine, bromine, iodine, or astatine. Specific examples of the (meth)acrylic acid halide include (meth)acrylic acid chloride, (meth)acrylic acid bromide, and (meth)acrylic acid iodide. Among these (meth)acrylic acid halides, (meth)acrylic acid chloride is preferred because of high reactivity and ease of availability.

A specific example of a method for producing a radically curable compound according to the present invention is a method that includes the following three steps.

(Step 1)

Cause polycondensation between the alkyl-substituted phenol (a1) and the aromatic aldehyde (a2) having a hydroxy group on a benzene ring in the presence of an acid catalyst to prepare a crude product containing the polycondensate (A) represented by the general formula (5) or the general formula (6) in a reaction solution.

(Step 2)

Collect from the reaction solution the polycondensate (A) prepared in the step 1.

(Step 3)

Cause a reaction between the polycondensate (A) isolated in the step 2 and the (meth)acrylic acid halide (B) in the presence of a base.

Examples of the acid catalyst used in the step 1 include acetic acid, oxalic acid, sulfuric acid, hydrochloric acid, phenolsulfonic acid, paratoluenesulfonic acid, zinc acetate, and manganese acetate. These acid catalysts may be used alone or in combination of two or more thereof. Of these acid catalysts, sulfuric acid and paratoluenesulfonic acid are preferred because of high activity. Note that such an acid catalyst may be added prior to the reaction or during the reaction.

In the step 1, if necessary, the polycondensate may be prepared in the presence of a solvent. Examples of the solvent include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxane, 1,4-dioxane, and tetrahydrofuran; glycol esters such as ethylene glycol acetate; and ketones such as acetone, methyl ethyl ketone, and methyl isobutyl ketone. These solvents may be used alone or in combination of two or more thereof. Among these solvents, 2-ethoxyethanol is preferred because the compound to be obtained is highly soluble therein.

In the step 1, the reaction temperature of polycondensation between the alkyl-substituted phenol (a1) and the aromatic aldehyde (a2) having a hydroxy group on a benzene ring is, for example, 60° C. to 140° C. The reaction time is, for example, 0.5 to 100 hours.

In the step 1, the charging ratio [(a1)/(a2)] (molar ratio) of the alkyl-substituted phenol (a1) to the aromatic aldehyde (a2) having a hydroxy group on a benzene ring is preferably in the range of 1/0.2 to 1/0.5, more preferably in the range of 1/0.25 to 1/0.45 because unreacted alkyl-substituted phenol is easily removed, the yield of the product is high, and the reaction product having a high purity can be obtained.

Examples of the polycondensate (A) obtained as a result of polycondensation of the step 1 include compounds represented by the following general formulae (3-1) to (3-10).

[Chem. 8]

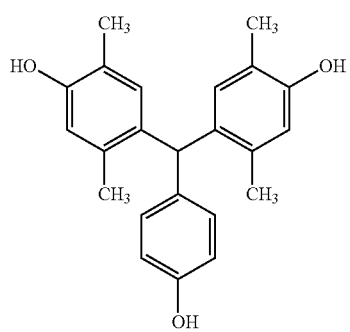
(3-1)

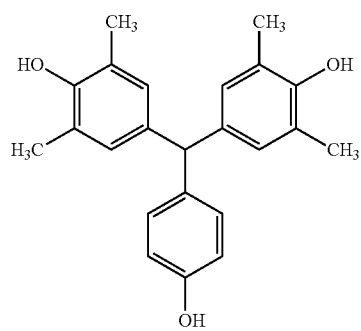
(3-2)

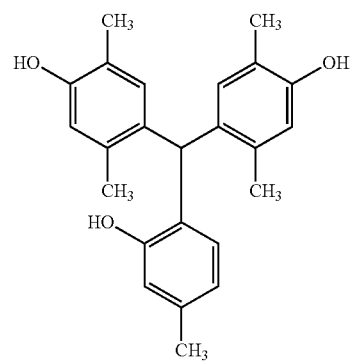
(3-3)

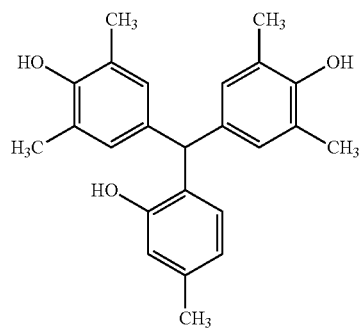
(3-4)

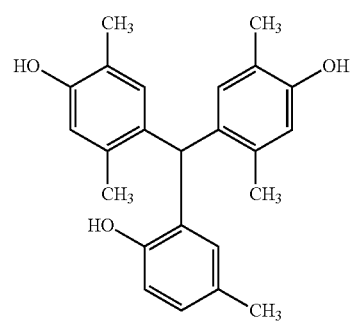
(3-5)

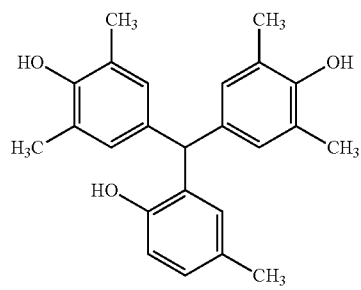
(3-6)

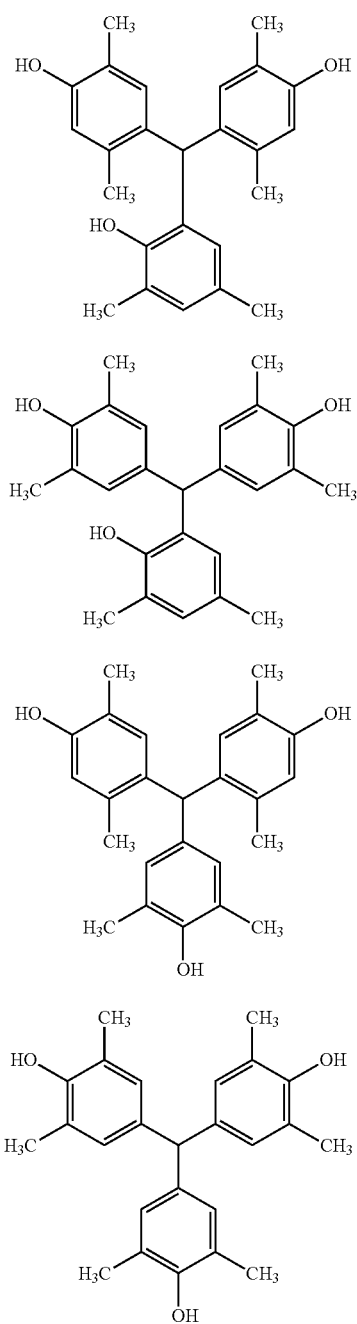

(3-7)
(3-8)
(3-9)
(3-10)

The reaction solution provided by the step 1 may contain, in addition to the polycondensate (A), unreacted compounds of the (a1), the (a2), or the like. Unwanted condensates may be generated that are not condensates having a structure represented by the general formula (5) or the general formula (6). In a case where such a reaction solution is subjected to a reprecipitation process with water to obtain a substance collected for a reaction with the (meth)acryloyl acid halide (B), this collected substance may contain, in addition to the target polycondensate (A), unreacted compounds of the (a1), the (a2), or the like or the unwanted polycondensates in a large amount.

For this reason, from the substance collected from the reaction solution in the step 2, the polycondensate (A) is preferably further collected to maximize the purity of the polycondensate (A).

The purity of the polycondensate (A) that is to react with the (meth)acryloyl acid halide (B) is preferably 85% or more, more preferably 90% or more, still more preferably 94% or more, particularly preferably 98% or more, and most preferably 100%. The purity of the polycondensate (A) can be determined on the basis of an area ratio in a gel permeation chromatography (GPC) chart.

In the present invention, the measurement conditions of GPC are as follows.

[GPC Measurement Conditions]

Measurement device: "HLC-8220 GPC" manufactured by Tosoh Corporation

Columns: "Shodex KF802" (8.0 mm ϕ×300 mm) manufactured by SHOWA DENKO K. K.

+"Shodex KF802" (8.0 mm ϕ×300 mm) manufactured by SHOWA DENKO K. K.

+"Shodex KF803" (8.0 mm ϕ×300 mm) manufactured by SHOWA DENKO K. K.

+"Shodex KF804" (8.0 mm ϕ×300 mm) manufactured by SHOWA DENKO K. K.

Column temperature: 40° C.

Detector: RI (differential refractometer)

Data processing: "GPC-8020 model II version 4.30" manufactured by Tosoh Corporation Developing solvent: tetrahydrofuran Flow rate: 1.0 ml/min Sample: obtained by filtering tetrahydrofuran solution having 0.5 mass % resin solid content through microfilter Injection amount: 0.1 ml Standard samples: monodisperse polystyrenes below (Standard Samples: Monodisperse Polystyrenes)

"A-500" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation In the step 2, impurities such as unreacted compounds of the (a1), the (a2), or the like are separated from the polycondensate (A), so that the resultant radically curable compound according to the present invention has high crystallinity. Thus, a radically curable compound according to the present invention tends to be closely packed. A radically curable compound according to the present invention in the state of being closely packed is cured. As a result, the molecular motion of the cured product is suppressed. Thus, the glass transition temperature becomes 400° C. or more and the heat resistance can be at least doubled, compared with existing cases.

The process of collecting the polycondensate (A) from the reaction solution in the step 2 can be performed, for example, in the following manner. The reaction solution is added into a poor solvent (S1) in which the reaction product is insoluble or slightly soluble and the resultant precipitate is separated by filtration. The precipitate is then dissolved in a solvent (S2) that can dissolve the reaction product therein and is compatible with the poor solvent (S1). This solution is added to the poor solvent (S1) again and the resultant precipitate is separated by filtration. Examples of the poor solvent (S1) used here include water; monoalcohols such as methanol, ethanol, and propanol; aliphatic hydrocarbons such as n-hexane, n-heptane, n-octane, and cyclohexane; and aromatic hydrocarbons such as toluene and xylene. Among these poor solvents (S1), water and methanol are preferred because removal of the acid catalyst can also be simultaneously achieved efficiently.

On the other hand, examples of the solvent (S2) include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxane and 1,4-dioxane; glycol esters such as ethylene glycol acetate; and ketones such as acetone, methyl ethyl ketone, and methyl isobutyl ketone. In a case where water is used as the poor solvent (S1), the (S2) is preferably acetone. Note that, regarding each of the poor solvent (S1) and the solvent (S2), a single solvent alone can be used or two or more solvents can be used in combination.

Examples of the base used in the step 3 include hydroxides of alkali metals such as sodium hydroxide and potassium hydroxide; carbonates of alkali metals such as sodium carbonate, potassium carbonate, and cesium carbonate; tertiary amines such as triethylamine and trimethylamine; and pyridine. Among the bases, preferred are potassium carbonate and tertiary amines and, in particular, more preferred are potassium carbonate and triethylamine because, after the reaction between the polycondensate (A) and the (meth)acrylic acid halide (B), such bases can be easily removed from the reaction system.

In the step 3, if necessary, a solvent may be used. Examples of the solvent include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxane, 1,4-dioxane, and tetrahydrofuran; glycol esters such as ethylene glycol acetate; and ketones such as acetone, methyl ethyl ketone, and methyl isobutyl ketone. These solvents may be used alone or in combination of two or more thereof. Among these solvents, preferred are tetrahydrofuran, methyl ethyl ketone, and methyl isobutyl ketone because the compound to be obtained is highly soluble therein.

In the step 3, the reaction temperature of the reaction between the polycondensate (A) and the (meth)acrylic acid halide (B) is, for example, 20° C. to 80° C. The reaction time is, for example, 1 to 30 hours.

In the step 3, regarding the charging ratio of the polycondensate (A) to the (meth)acrylic acid halide (B), a molar ratio [(A')/(B)] where A' represents the number of moles of phenolic hydroxy groups of the polycondensate (A) is preferably in the range of 1/1 to 1/3, more preferably in the range of 1/1 to 1/2.5 because a radically curable compound according to the present invention can be obtained with a high purity and with a high yield.

A radically curable composition according to the present invention contains the above-described radically curable compound according to the present invention as an essential component. The radically curable composition may contain the above-described radically curable compound according to the present invention alone or may further contain another radically curable compound.

Examples of the other radically curable compound used herein may include various epoxy (meth)acrylates and other (meth)acrylate compounds.

The epoxy (meth)acrylates may be obtained by, for example, subjecting various polyglycidyl ether compounds to an addition reaction with (meth)acrylic acid or a halide of (meth)acrylic acid. Examples of the various polyglycidyl ethers include polyglycidyl ethers of aromatic polyols such as hydroquinone, 2-methylhydroquinone, 1,4-benzenedimethanol, 3,3'-biphenol, 4,4'-biphenol, tetramethylbiphenol, biphenyl-3,3'-dimethanol, biphenyl-4,4'-dimethanol, bisphenol A, bisphenol B, bisphenol F, bisphenol S, 1,4-naphthalenediol, 1,5-naphthalenediol, 1,6-naphthalenediol, 2,6-naphthalenediol, 2,7-naphthalenediol, naphthalene-2,6-dimethanol, and 4,4',4"-methylidinetrisphenol;

polyglycidyl ethers of polyether-modified aromatic polyols obtained by ring-opening polymerization between the above-described aromatic polyols and various cyclic ether compounds such as ethylene oxide, propylene oxide, tetrahydrofuran, ethyl glycidyl ether, propyl glycidyl ether, butyl glycidyl ether, phenyl glycidyl ether, or allyl glycidyl ether;

polyglycidyl ethers of lactone-modified aromatic polyols obtained by polycondensation between the above-described aromatic polyols and lactone compounds such as ε-caprolactone;

polyglycidyl ethers of aromatic-ring-containing polyester polyols obtained by a reaction between aliphatic dicarboxylic acids such as malonic acid, succinic acid, glutaric acid, adipic acid, or pimelic acid and the above-described aromatic polyols;

polyglycidyl ethers of aromatic-ring-containing polyester polyols obtained by a reaction between aromatic dicarboxylic acids or anhydrides thereof such as phthalic acid, phthalic anhydride, terephthalic acid, isophthalic acid, or orthophthalic acid, and aliphatic polyols such as aliphatic polyols such as ethylene glycol, diethylene glycol, propylene glycol, 1,3-propanediol, 1,4-butanediol, 1,3-butanediol, 3-methyl-1,3-butanediol, 1,5-pentanediol, neopentyl glycol, 1,6-hexanediol, trimethylolethane, trimethylolpropane, or glycerin;

bisphenol type epoxy resins such as bisphenol A type epoxy resins, bisphenol B type epoxy resins, bisphenol F type epoxy resins, and bisphenol S type epoxy resins; and novolac type epoxy resins such as phenol novolac type epoxy resins and cresol novolac type epoxy resins. These resins may be used alone or in combination of two or more thereof.

Examples of the above-described other (meth)acrylate compounds include monofunctional (meth)acrylate compounds such as n-butyl (meth)acrylate, isobutyl (meth)acrylate, tert-butyl (meth)acrylate, n-pentyl (meth)acrylate, n-hexyl (meth)acrylate, n-octyl (meth)acrylate, isooctyl (meth)acrylate, 2-ethylhexyl (meth)acrylate, benzyl (meth)acrylate, phenoxyethyl (meth)acrylate, phenoxydiethylene glycol (meth)acrylate, glycidyl (meth)acrylate, morpholine (meth)acrylate, 2-hydroxyethyl (meth)acrylate, 2-hydroxypropyl (meth)acrylate, 4-hydroxybutyl (meth)acrylate, diethylene glycol mono(meth)acrylate, triethylene glycol mono(meth)acrylate, dipropylene glycol mono(meth)acrylate, 2-methoxyethyl (meth)acrylate, methoxydiethylene glycol (meth)acrylate, methoxytriethylene glycol (meth)acrylate, methoxypolyethylene glycol (meth)acrylate, 2-butoxyethyl (meth)acrylate, butoxytriethylene glycol (meth)acrylate, 2-ethoxyethyl (meth)acrylate, 2-(2-ethoxyethoxy)ethyl (meth)acrylate, ethoxypolyethylene glycol (meth)acrylate, 4-nonylphenoxy ethylene glycol (meth)acrylate, tetrahydrofurfuryl (meth)acrylate, caprolactone-modified tetrahydrofurfuryl (meth)acrylate, cyclohexyl (meth)acrylate, isobornyl (meth)acrylate, 2-hydroxy-3-phenoxypropyl (meth)acrylate, cyclohexyl (meth)acrylate, cyclohexylmethyl (meth)acrylate, cyclohexylethyl (meth)acrylate, dicyclopentanyl (meth)acrylate, dicyclopentanyloxyethyl (meth)acrylate, dicyclopentenyl (meth)acrylate, dicyclopentenyloxyethyl (meth)acrylate, phenylbenzyl (meth)acrylate, and phenylphenoxyethyl acrylate;

di(meth)acrylate compounds such as ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, tripropylene glycol di(meth)acrylate, butylene glycol di(meth)acrylate, tetrabutylene glycol di(meth)acrylate, 1,4-butanediol di(meth)acrylate, 1,6-hexanediol di(meth)acrylate, 1,9-nonanediol di(meth)acrylate, neopentyl glycol di(meth)acrylate, di(meth)acrylate of ethylene oxide adduct of bisphenol A, di(meth)acrylate of propylene oxide adduct of bisphenol A, di(meth)acrylate of ethylene oxide adduct of bisphenol F, di(meth)acrylate of propylene oxide adduct of bisphenol F, dicyclopentanyl di(meth)acrylate, glycerol di(meth)acrylate, neopentyl glycol hydroxypivalic acid ester di(meth)acrylate, caprolactone-modified hydroxypivalic acid neopentyl glycol di(meth)acrylate, tetrabromobisphenol A di(meth)acrylate, hydropivalaldehyde-modified trimethylolpropane di(meth)acrylate, 1,4-cyclohexanedimethanol di(meth)acrylate, and bis[(meth)acryloylmethyl]biphenyl; and (meth)acrylate compounds having a functionality of three or more such as trimethylolpropane tri(meth)acrylate, tri(meth)acrylate of ethylene oxide adduct of trimethylolpropane, tri(meth)acrylate of propylene oxide adduct of trimethylolpropane, pentaerythritol tri(meth)acrylate, glycerol tri(meth)acrylate, tri(meth)acrylate of alkyl-modified dipentaerythritol, ditrimethylolpropane tetra(meth)acrylate, tetra(meth)acrylate of ethylene oxide adduct of ditrimethylolpropane, tetra(meth)acrylate of propylene oxide adduct of ditrimethylolpropane, penta(meth)acrylate of dipentaerythritol, and hexa(meth)acrylate of dipentaerythritol. These compounds may be used alone or in combination of two or more thereof.

The radically curable composition contains the above-described radically curable compound according to the present invention in an amount as long as an advantage of the present invention, that is, high heat resistance of cured products, is achieved. Specifically, a radically curable compound according to the present invention is preferably used alone; or, with respect to 100 parts by mass of the total of a radically curable compound according to the present invention and another radically curable compound, the content of the radically curable compound according to the present invention is preferably 50 parts by mass or more, more preferably 80 parts by mass or more.

A radically curable composition according to the present invention may further contain a polymerization initiator and can be cured by irradiation with an active energy ray or by heating to thereby provide a cured product.

In a case where a radically curable composition according to the present invention is cured through radical polymerization by irradiation with an active energy ray, the polymerization initiator used is an intramolecular-cleavage-type photopolymerization initiator or a hydrogen-abstraction-type photopolymerization initiator.

Examples of the intramolecular-cleavage-type photopolymerization initiator include acetophenone-based compounds such as 1-hydroxycyclohexyl phenyl ketone, diethoxyacetophenone, 2-hydroxy-2-methyl-1-phenylpropan-1-one, benzyldimethylketal, 1-(4-isopropylphenyl)-2-hydroxy-2-methylpropan-1-one, 4-(2-hydroxyethoxy)phenyl-(2-hydroxy-2-propyl)ketone, 2-methyl-2-morpholino(4-thiomethylphenyl)propan-1-one, and 2-benzyl-2-dimethylamino-1-(4-morpholinophenyl)-butanone;

benzoins such as benzoin, benzoin methyl ether, and benzoin isopropyl ether; acyl phosphine oxide-based compounds such as 2,4,6-trimethylbenzoindiphenylphosphine oxide and bis(2,4,6-trimethylbenzoyl)-phenylphosphine oxide; azo compounds such as 1,1'-azobisisobutyronitrile, 1,1'-azobiscyclohexanecarbonitrile, and 2-cyano-2-propylazoformamide; benzil, and methyl phenylglyoxylate.

Examples of the hydrogen-abstraction-type photopolymerization initiator include benzophenone-based compounds such as benzophenone, methyl o-benzoylbenzoate-4-phenylbenzophenone, 4,4'-dichlorobenzophenone, hydroxybenzophenone, 4-benzoyl-4'-methyl-diphenylsulfide, acrylated benzophenone, 3,3',4,4'-tetra(t-butylperoxycarbonyl)benzophenone, and 3,3'-dimethyl-4-methoxybenzophenone; thioxanthone-based compounds such as 2-isopropylthioxanthone, 2,4-dimethylthioxanthone, 2,4-diethylthioxanthone, and 2,4-dichlorothioxanthone; aminobenzophenone-based compounds such as Michler's ketone and 4,4'-diethylaminobenzophenone; 10-butyl-2-chloroacridone, 2-ethylanthraquinone, 9,10-phenanthrenequinone, and camphorquinone.

Among the above-described photopolymerization initiators, preferred are acetophenone-based compounds such as 1-hydroxycyclohexyl phenyl ketone, 2-hydroxy-2-methyl-1-phenylpropan-1-one, 1-(4-isopropylphenyl)-2-hydroxy-2-methylpropan-1-one, 4-(2-hydroxyethoxy)phenyl-(2-hydroxy-2-propyl)ketone, 2-methyl-2-morpholino(4-thiomethylphenyl)propan-1-one, and 2-benzyl-2-dimethylamino-1-(4-morpholinophenyl)-butanone, and benzophenone. In particular, 1-hydroxycyclohexyl phenyl ketone is preferred. Such photopolymerization initiators may be used alone or in combination of two or more thereof.

The amount of such a photopolymerization initiator used with respect to 100 parts by mass of a radically curable composition according to the present invention is preferably 0.01 to 20 parts by mass, more preferably 0.1% to 15% by mass, still more preferably 0.5 to 10 parts by mass. Note that, in a case where an electron beam described below is used as an active energy ray, use of photopolymerization initiators is not necessary.

Examples of an active energy ray used for curing a radically curable composition according to the present invention include ionizing radiations such as ultraviolet rays, electron beams, α-rays, β-rays, and γ-rays. Examples of energy sources or curing devices that generate such active energy rays include a germicidal lamp, an ultraviolet lamp (black light), carbon arc, a xenon lamp, a high-pressure mercury lamp for copying, a medium- or high-pressure mercury lamp, an ultra-high-pressure mercury lamp, an electrodeless lamp, a metal halide lamp, ArF excimer laser, an ultraviolet LED, ultraviolet rays from a light source such as natural light, and electron beams from a scanning-type or curtain-type electron beam accelerator.

In a case where a radically curable composition according to the present invention is cured by thermal radical polymerization, a thermal radical polymerization initiator is used. Examples of the thermal radical polymerization initiator include organic peroxides such as benzoyl peroxide, di-t-butyl peroxide, dicumyl peroxide, 3,3,5-trimethylhexanoyl peroxide, di-2-ethylhexylperoxy dicarbonate, methyl ethyl ketone peroxide, t-butyl peroxyphthalate, t-butyl peroxybenzoate, di-t-butyl peroxyacetate, t-butyl peroxyisobutyrate, t-butyl peroxy-2-hexanoate, and t-butyl peroxy-3,3,5-trimethylhexanoate; and azo compounds such as 1,1'-azobisisobutyronitrile, 1,1'-azobiscyclohexanecarbonitrile, and 2-cyano-2-propylazoformamide. Among these thermal radical polymerization initiators, preferred are benzoyl peroxide and 1,1'-azobisisobutyronitrile. These thermal radical polymerization initiators may be used alone or in combination of two or more thereof.

The amount of such a thermal radical polymerization initiator used with respect to 100 parts by mass of a radically curable composition according to the present invention is preferably 0.01 to 20 parts by mass, more preferably 0.1% to 15% by mass, still more preferably 0.5 to 10 parts by mass.

EXAMPLES

Hereinafter, the present invention will be described further in detail with reference to specific examples. Note that an NMR spectrum measurement method used for identifying compounds is as follows.

[¹H-NMR Spectrum Measurement Method]

JNM-GSX500 (500 MHz, DMSO-d6, TMS) manufactured by JEOL Ltd. was used to carry out a structural analysis.

Synthesis Example 1

Synthesis of Polycondensate (A-1)

To a 100-ml two-neck flask equipped with a condenser, 7.32 g (60 mmol) of 2,5-xylenol and 2.44 g (20 mmol) of 4-hydroxybenzaldehyde were charged and dissolved in 20 ml of 2-ethoxyethanol. To this solution being cooled in an ice bath, 2 ml of sulfuric acid was added. The resultant solution was heated and stirred in an oil bath at 100° C. for 2 hours to thereby cause a reaction. After the reaction, the resultant solution was subjected to a reprecipitation process with water to provide a crude product. The crude product was dissolved again in acetone and subjected to a reprecipitation process with water. The resultant product was isolated by filtration and subjected to vacuum drying. This provided 5.93 g of a polycondensate (A-1) having a molecular structure represented by a formula (5-1) below. The purity of the polycondensate (A-1) in the crude product was 87% by mass on the basis of GPC area ratio. The purity of the polycondensate (A-1) finally obtained was 99% by mass.

[Chem. 9]

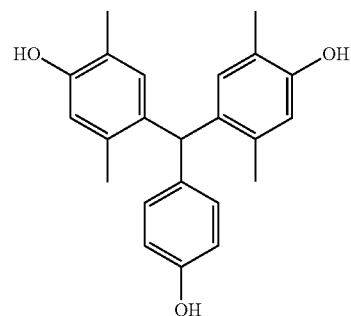

(5-1)

Example 1

Synthesis of Radically Curable Compound

To a 100-ml two-neck flask equipped with a condenser, 1.74 g (5 mmol) of the polycondensate (A-1), 4.10 g (30 mmol) of potassium carbonate, and 10 ml of tetrahydrofuran were charged and stirring was initiated. To this solution being cooled in an ice bath, 3.60 g (20 mmol) of acryloyl chloride was added dropwise over 30 minutes. The resultant solution was heated and stirred in an oil bath at 70° C. for 12 hours to thereby cause a reaction. After the reaction, solid content was separated from the resultant solution by filtration; the filtrate was mixed with 30 ml of chloroform and washed three times with 50 ml of water. The underlying organic layer was separated and dried over sodium sulfate. After that, the solvent was distilled off under a reduced pressure to provide 1.79 g of a radically curable compound (1) that was white acicular crystals. This compound was identified on the basis of peaks of 1H-NMR and it was confirmed that the compound represented by a structural formula (3-1) was obtained at a purity of 100%. FIG. 1 is the chart of the ¹H-NMR spectrum.

[Chem. 10]

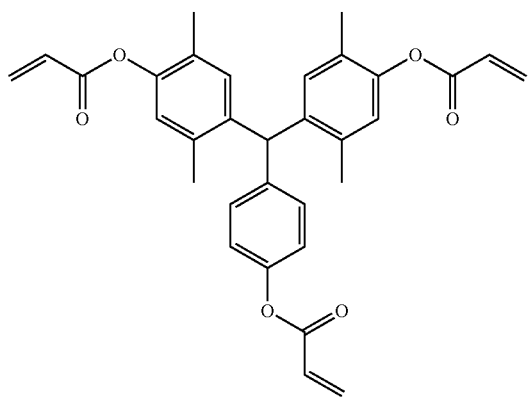

(3-1)

The spectral peak values of the ¹H-NMR spectrum are as follows.

[¹H-NMR Spectrum]

(ppm, 500 MHz, solvent: DMSO-d₆, standard: TMS)

1.9-2.2 (12H; Ar—C$\underline{H_3}$), 5.6-5.8 (1H; Ar—C$\underline{H}$), 6.1-6.3 (3H; C-C$\underline{H_2}$), 6.4-6.5 (3H; CO—C$\underline{H}$—C), 6.5-6.6 (2H; Ar), 6.6-6.7 (3H; C—C$\underline{H_2}$), 6.9-7.3 (6H; $\underline{Ar}$)

Comparative Synthesis Example 1

Synthesis of Bisphenol A (BPA) Type Epoxy Acrylate

A reaction between 188 parts by mass of a bisphenol A (BPA) type liquid epoxy resin ("EPICLON850" manufactured by DIC Corporation; epoxy equivalent weight: 188 g/eq.) and 72% by mass of acrylic acid (in a ratio so as to satisfy number of epoxy groups:total number of carboxyl groups=1:1) was caused at 95° C. to provide 253 parts by mass of a BPA type epoxy acrylate that was a transparent viscous liquid.

Comparative Synthesis Example 2

Synthesis of Tetramethylbiphenyl Type Epoxy Acrylate

A reaction between 195 parts by mass of a tetramethylbiphenyl type liquid epoxy resin ("JER YX-4000H" manufactured by Mitsubishi Chemical Corporation; epoxy equivalent weight: 195 g/eq.) and 72 parts by mass of acrylic acid (in a ratio so as to satisfy number of epoxy groups:total number of carboxyl groups=1:1) was caused at 95° C. to provide 264 parts by mass of a tetramethylbiphenyl type epoxy acrylate that was a transparent viscous liquid.

Comparative Synthesis Example 3

Synthesis of Cresol Novolac Type Epoxy Acrylate

A reaction between 214 parts by mass of an o-cresol novolac type epoxy resin ("EPICLON N-695" manufactured by DIC Corporation; epoxy equivalent weight: 214 g/eq.) and 72 parts by mass of acrylic acid (in a ratio so as to satisfy number of epoxy groups:total number of carboxyl groups=1: 1) was caused at 100° C. to provide 273 parts by mass of a cresol novolac type epoxy acrylate that was a yellow solid.

Test Examples 1 and 2 and Comparative Test Examples 1 to 6

The acrylates obtained in Example 1 and Comparative synthesis examples 1 to 3 above were used to prepare cured products in Test examples 1 and 2 and Comparative test examples 1 to 6. The glass transition temperature of each cured product was measured and the heat resistance of the cured product was evaluated by a method described below. The results are described in Table 1.

Test Example 1

The radically curable compound (1) (0.50 g) obtained in Example 1, 0.05 g of IRGACURE 184 [manufactured by Ciba Specialty Chemicals], and 0.5 g of tetrahydrofuran were placed into a Schlenk tube and subjected to freeze-drying in a nitrogen atmosphere. This reaction vessel was sealed and irradiated for 3 hours with light from a high-pressure mercury lamp equipped with a 340 nm band-pass filter. The resultant content was subjected to a reprecipitation process with methanol. The resultant precipitate was subjected to filtration and vacuum drying to provide 0.35 g of a polymer (a). The obtained polymer (a) was subjected to a DSC measurement to perform evaluation in terms of heat resistance (Tg).

Test Example 2

The radically curable compound (1) (0.50 g) obtained in Example 1, 0.05 g of azobisisobutyronitrile [AIBN; reagent manufactured by Wako Pure Chemical Industries, Ltd.], and 0.5 g of dichloroethane were placed into a Schlenk tube and subjected to freeze-drying in a nitrogen atmosphere. This reaction vessel was sealed and a reaction was caused at 70° C. for 12 hours. The resultant content was subjected to a reprecipitation process with methanol. The resultant precipitate was subjected to filtration and vacuum drying to provide 0.21 g of a polymer (b). The obtained polymer (b) was subjected to a DSC measurement to perform evaluation in terms of heat resistance (Tg).

Comparative Example 1

The same processes were performed as in Example 2 except that the radically curable compound (1) in Example 2 was replaced by the BPA type epoxy acrylate obtained in Comparative synthesis example 1. Thus, 0.23 g of a cured product of the BPA type epoxy acrylate was obtained. As in Test example 1, evaluation in terms of heat resistance (Tg) was performed.

Comparative Example 2

The same processes were performed as in Example 3 except that the radically curable compound (1) in Example 3 was replaced by the BPA type epoxy acrylate obtained in Comparative synthesis example 1. Thus, 0.13 g of a cured product of the BPA type epoxy acrylate was obtained. As in Test example 1, evaluation in terms of heat resistance (Tg) was performed.

Comparative Example 3

The same processes were performed as in Example 2 except that the radically curable compound (1) in Example 2 was replaced by the tetramethylbiphenyl type epoxy acrylate obtained in Comparative synthesis example 2. Thus, 0.35 g of a cured product of the tetramethylbiphenyl type epoxy acrylate was obtained. As in Test example 1, evaluation in terms of heat resistance (Tg) was performed.

Comparative Example 4

The same processes were performed as in Example 3 except that the radically curable compound (1) in Example 3 was replaced by the tetramethylbiphenyl type epoxy acrylate obtained in Comparative synthesis example 2. Thus, 0.33 g of a cured product of the tetramethylbiphenyl type epoxy acrylate was obtained. As in Test example 1, evaluation in terms of heat resistance (Tg) was performed.

Comparative Example 5

The same processes were performed as in Example 2 except that the radically curable compound (1) in Example 2 was replaced by the cresol novolac type epoxy acrylate obtained in Comparative synthesis example 3. Thus, 0.37 g of a cured product of the cresol novolac type epoxy acrylate was obtained. As in Test example 1, evaluation in terms of heat resistance (Tg) was performed.

Comparative Example 6

The same processes were performed as in Example 3 except that the radically curable compound (1) in Example 3 was replaced by the cresol novolac type epoxy acrylate obtained in Comparative synthesis example 3. Thus, 0.42 g of a cured product of the cresol novolac type epoxy acrylate was obtained. As in Test example 1, evaluation in terms of heat resistance (Tg) was performed.

[Method of Measuring Glass Transition Temperature of Cured Product]

A differential scanning calorimeter ("differential scanning calorimeter (DSC) Q100" manufactured by TA Instruments) was used to measure a glass transition temperature (hereafter abbreviated as "Tg") in a nitrogen atmosphere in a temperature range of 25° C. to 450° C. at a temperature increase rate of 10° C./min.

[Evaluation of Cured Product in Terms of Heat Resistance]

On the basis of Tg temperatures determined in the above-described measurements, evaluation in terms of heat resistance was performed in accordance with the following criteria.

Excellent: Tg is 300° C. or more
Good: Tg is 250° C. or more and less than 300° C.
Fair: Tg is 200° C. or more and less than 250° C.
Poor: Tg is less than 200° C.

Table 1 summarizes the raw materials cured into the cured products in Examples 2 and 3 and Comparative examples 1 to 6 above and results of Tg values and heat resistance evaluation. Note that ">400" of Tg of Examples 2 and 3 means that thermal decomposition occurs at a temperature higher than 400° C. without observation of glass transition temperature.

The results in Table 1 indicate the following: the cured products (Test examples 1 and 2) of the radically curable compound according to the present invention obtained in Example 1 thermally decompose at temperatures higher than 400° C. without observation of glass transition temperature and hence have very high heat resistance.

On the other hand, the cured products of existing epoxy acrylates that have been considered to have high heat resistance in Comparative examples 1 to 6 have Tg of 158° C. to 229° C., which are inferior to in terms of heat resistance the cured products of the radically curable compound according to the present invention.

The invention claimed is:

1. A radically curable compound represented by a general formula (1) below

[Chem. 1]

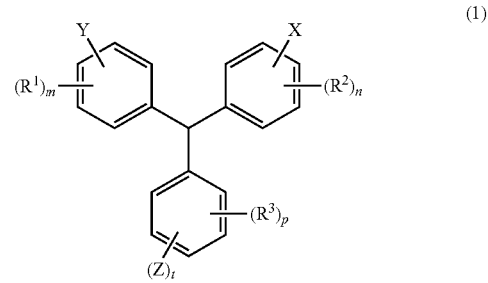

(1)

where $R^1$, $R^2$, and $R^3$ each independently represent an alkyl group having 1 to 8 carbon atoms; m and n each independently represent an integer of 1 to 4; p represents an integer of 0 to 4; X, Y, and Z each independently represent an acryloyloxy group or a methacryloyloxy group; and t represents 1 or 2.

2. A radically curable compound represented by a general formula (2) below

TABLE 1

|  |  | Test example 1 | Test example 2 | Comparative test example 1 | Comparative test example 2 | Comparative test example 3 | Comparative test example 4 | Comparative test example 5 | Comparative test example 6 |
|---|---|---|---|---|---|---|---|---|---|
| Components (g) | Radically curable compound | 0.5 | 0.5 |  |  |  |  |  |  |
|  | BPA type epoxy acrylate |  |  | 0.5 | 0.5 |  |  |  |  |
|  | Tetramethylbiphenyl type epoxy acrylate |  |  |  |  | 0.5 | 0.5 |  |  |
|  | Cresol novolac type epoxy acrylate |  |  |  |  |  |  | 0.5 | 0.5 |
|  | IRGACURE 184 | 0.05 |  | 0.05 |  | 0.05 |  | 0.05 |  |
|  | AIBN |  | 0.01 |  | 0.01 |  | 0.01 |  | 0.01 |
| Curing method |  | Photo curing | Thermal curing | Photo curing | Thermal curing | Photo curing | Thermal curing | Photo curing | Thermal curing |
| Evaluation results | Tg (° C.) | >400 | >400 | 158 | 163 | 171 | 178 | 221 | 229 |
|  | Heat resistance | Excellent | Excellent | Poor | Poor | Poor | Poor | Fair | Fair |

[Chem. 2]

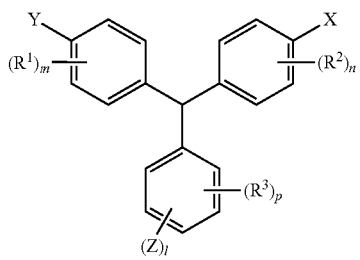

(2)

where $R^1$, $R^2$, and $R^3$ each independently represent an alkyl group having 1 to 8 carbon atoms; m and n each independently represent an integer of 1 to 4; p represents an integer of 0 to 4; and X, Y, and Z each independently represent an acryloyloxy group, a methacryloyloxy group, or a hydroxy group, and at least one of X, Y, and Z represents an acryloyloxy group or a methacryloyloxy group; and t represents 1 or 2, wherein at least one hydroxyl group is not in the ortho-position with respect to the center.

3. The radically curable compound according to claim 1, wherein $R^1$, $R^2$, and $R^3$ above each represent a methyl group.

4. A radically curable compound represented by a general formula (1) below

[Chem. 1]

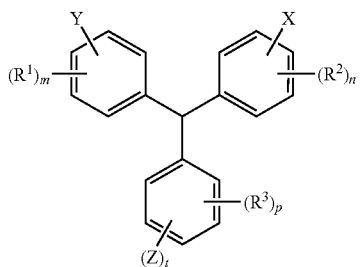

(1)

where $R^1$, $R^2$, and $R^3$ each independently represent an alkyl group having 1 to 8 carbon atoms; m, n, and p each independently represent an integer of 1 to 3; X, Y, and Z each independently represent an acryloyloxy group, a methacryloyloxy group, or a hydroxy group, and at least one of X, Y, and Z represents an acryloyloxy group or a methacryloyloxy group; and t represents 1 or 2, wherein at least one hydroxyl group is not in the ortho-position with respect to the center.

5. A radically curable composition comprising the radically curable compound according to claim 1.

6. A cured product obtained by curing the radically curable composition according to claim 5 with an active energy ray or heat.

7. A resist-material composition comprising the radically curable composition according to claim 5.

8. A radically curable composition comprising the radically curable compound according to claim 2.

9. A radically curable composition comprising the radically curable compound according to claim 3.

10. A radically curable composition comprising the radically curable compound according to claim 4.

11. A cured product obtained by curing the radically curable composition according to claim 8 with an active energy ray or heat.

12. A radically curable compound represented by a general formula (1) below

[Chem. 1]

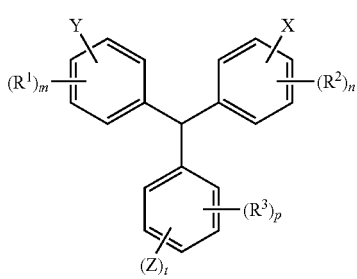

(1)

where $R^1$, $R^2$, and $R^3$ each independently represent an alkyl group having 1 to 8 carbon atoms; m and n each independently represent an integer of 1 to 4; p represents an integer of 0 to 4; X, Y, and Z each independently represent an acryloyloxy group, a methacryloyloxy group, or a hydroxy group, and only one of X, Y, and Z represents a hydroxy group; and t represents 1 or 2, wherein the hydroxyl group is not in the ortho-position with respect to the center.

13. The radically curable compound according to claim 2, wherein $R^1$, $R^2$, and $R^3$ above each represent a methyl group.

14. The radically curable compound according to claim 4, wherein $R^1$, $R^2$, and $R^3$ above each represent a methyl group.

15. The radically curable compound according to claim 12, wherein $R^1$, $R^2$, and $R^3$ above each represent a methyl group.

16. A radically curable composition comprising the radically curable compound according to claim 12.

17. A resist-material composition comprising the radically curable composition according to claim 8.

18. A resist-material composition comprising the radically curable composition according to claim 10.

19. A resist-material composition comprising the radically curable composition according to claim 13.

20. A resist-material composition comprising the radically curable composition according to claim 14.

* * * * *